United States Patent

Kunisaki et al.

[11] Patent Number: 5,876,489
[45] Date of Patent: Mar. 2, 1999

[54] GERM-REMOVING FILTER AND APPARATUS FOR MAINTAINING STERILE ROOM UNDER STERILE CONDITION

[75] Inventors: Shinichi Kunisaki; Takeshi Saeki; Goro Fujiwara; Mitsunobu Masuda; Takeshi Morimoto, all of Osaka, Japan

[73] Assignees: Suntory Limited; Takuma Co., Ltd, both of Osaka, Japan

[21] Appl. No.: 610,733

[22] Filed: Mar. 5, 1996

[30] Foreign Application Priority Data

Mar. 6, 1995 [JP] Japan ................................. 7-045179

[51] Int. Cl.$^6$ .......................... B01D 39/16; B01D 50/00
[52] U.S. Cl. ........................... 96/226; 55/385.2; 55/485; 55/524
[58] Field of Search .............................. 55/279, 318, 327, 55/385.2, 485, 524; 95/285, 287; 422/122; 454/53; 96/226; 210/501, 505, 508

[56] References Cited

U.S. PATENT DOCUMENTS 5,496,860  3/1996  Matsumoto et al. ...................... 521/31
5,626,820  5/1997  Kinkead et al. ......................... 422/122

FOREIGN PATENT DOCUMENTS 279085   4/1929  United Kingdom .
1564413  4/1980  United Kingdom .

*Primary Examiner*—Ivars Cintins
*Attorney, Agent, or Firm*—Webb Ziesenheim Bruening Logsdon Orkin & Hanson, P.C.

[57] ABSTRACT

A germ-removing filter includes a filter substrate, and an antimicrobial material dispersedly mixed into the filter substrate. The antimicrobial material is antimicrobial fiber bonded with silver ion. The total amount of the silver ions present in the filter substrate material when mixed with the antimicrobial fiber is equivalent to an amount of silver ions contained in an antimicrobial fiber which is mixed at more than 10 wt % in the filter substrate and which has entire exchange groups or bonding groups thereof exchanged or bonded with silver ions. An apparatus using the filter for maintaining a sterile room under sterile condition is also disclosed.

12 Claims, 3 Drawing Sheets

GERM-REMOVING FILTER AND APPARATUS FOR MAINTAINING STERILE ROOM UNDER STERILE CONDITION

BACKGROUND OF THE INVENTION

1. Field of the Invention

The present invention relates to a germ-removing filter for sterilizing air to be supplied into a sterile room (bioclean room) used in e.g. manufacture of food products, medical products, breeding and/or germ-free experiments of laboratory animals, in particular a sterile room in a hospital and relates also to an apparatus using the germ-removing filter for maintaining the sterile room under the sterile condition.

2. Description of the Related Art

The convention has proposed following means for maintaining a sterile room under a sterile condition;

According to the first method, living germs as a kind of fine particles are removed together with dust by a HEPA filter (high performance filter) and also a chemical sterilizing treatment such as a fumigation is effected on the sterile room periodically or non-periodically. In short, the HEPA filter is utilized as a germ-removing filter.

According to the second method, as a HEPA filter to be incorporated within an air supply passage extending to a sterile room, there is used a HEPA filter provided with antimicrobial property by mixing silver zeolite particles as antimicrobial material to a filter substrate at more than 5 g per 1 $m^2$ of filtering area. This filter is rendered antimicrobial by uniformly mixing silver zeolite particles and binder in the filter substrate in the paper making process of the filter substrate.

According to the third method, as a HEPA filter to be incorporated within an air supply passage extending to a sterile room, there are used threads woven with uniformly mixing silver zeolite particles in synthetic resin fiber. More particularly, this filter uses, as the filter substrate thereof, a non-woven fabric which is formed by causing silver zeolite particles to be uniformly dispersed in a fiber-forming bath of synthetic fiber.

The above-described conventional methods suffer problems to be described next.

The first method inevitably invites formation of pores in the HEPA filter. Thus, the filter is unreliable in its germ-removing effect. Accordingly, for reliably maintaining the sterile room under sterile condition, this method additionally requires the chemical sterilizing treatment using a chemical sterilizing agent. Further, as the sterilizing effect depends mainly on this chemical treatment, it is impossible for this method to achieve complete sterile condition.

In addition, although the living germs may be entrapped within the HEPA filter, these entrapped living germs are stuck within the filter and may proliferate rapidly here due to e.g. variation in humidity. And, these proliferated germs are quite likely to invade the exit or transmission side of the filter through the pores.

In summary, in the case of the first method, although a HEPA filter is employed as a germ-removing filter, this filter is poor in its germ removing performance, so that the sterile room cannot be maintained under sterile condition.

In the case of the second method, since the silver zeolite particles mixed in the filter substrate are very fine particles ranging in diameter about 2 μm on the average, the very presence of such super fine particles within the filter substrate may be detrimental to the original, fine-particle entrapping function of the HEPA filter.

Moreover, the silver zeolite fine particles dispersed and stuck to the surface of the filter substrate via the binder will inevitably fall out therefrom. Hence, there is very high possibility of dust generation due to such fallout of silver zeolite particles. For this reason, the chances are high for the significant deterioration in the original function of the HEPA filter and the deterioration is also inevitable in the antimicrobial effect with passage of time.

On the other hand, if a greater amount of binder were used in order to restrict fallout of the silver zeolite particles, the possibility would increase that the binder would cover the silver zeolite particles entirely. As a result, the method will not be able to provide the filter with the intended antimicrobial effect in spite of the addition thereto of the silver zeolite particles.

In short, with the second method, although this method intends to improve the germ-removing effect through prevention of proliferation of germs within the HEPA filter by providing this filter with the antimicrobial property, this filter cannot provide the antimicrobial effect in a reliable manner. So that, the germs inevitably leak to the transmission side of the filter, and therefore, this method too cannot provide satisfactory germ-removing effect.

In the case of the third method, the silver zeolite particles employed comprise fine particles ranging in diameter about 2 μm on the average as described hereinbefore. On the other hand, the synthetic fiber filament, into which the silver zeolite particles are mixed, have the diameter of 8–15 μm. Accordingly, the possibility is rather low for the entire silver zeolite particles to come out on the surface of the synthetic fiber filament. As a result, this filter can only provide rather limited antimicrobial effect, considering the amount of the silver zeolite particles mixed into the filter substrate. Moreover, there is significant irregularity in the amount of the silver zeolite particles coming out to the surface of the synthetic fiber filament. Accordingly, with this filter, it is difficult to obtain stable antimicrobial effect.

In conclusion, with this third method too, although the method intends to improve the germ-removing effect through prevention of proliferation of germs within the HEPA filter by providing this filter with the antimicrobial property, this filter cannot provide the antimicrobial effect in a reliable manner. So that, the germs inevitably leak to the transmission side of the filter, and therefore, this method too cannot provide satisfactory germ-removing effect.

In view of the above-described state of the art, a first object of the present invention is to provide a germ-removing filter which can remove germs reliably.

A second object of the invention is to provide a germ-removing filter which can provide improved germ-entrapping rate, in addition to the improved reliability.

A third object of the invention is to effectively utilize the above-described, germ-removing filter to prevent invasion of living germs into a sterile room through an air supply passage or an air exhaust passage extending to the sterile room.

A fourth object of the invention is to effectively utilize the above-described, germ-removing filter to prevent invasion of living germs into a sterile room through an air supply passage extending thereto in a system where the air supply passage incorporates therein a HEPA filter for filtering the air to be supplied to the sterile room.

SUMMARY OF THE INVENTION

For accomplishing the above-noted object, a germ-removing filter, according to the first invention, comprises:

a filter substrate:

an antimicrobial material dispersedly mixed into the filter substrate, the antimicrobial material comprising antimicrobial fiber bonded with silver ion;

wherein the total amount of the silver ions present in the filter substrate material when mixed with the antimicrobial fiber is equivalent to an amount of silver ions contained in an antimicrobial fiber which is mixed at more than 10 wt % in the filter substrate and which has entire exchange groups or bonding groups thereof exchanged or bonded with silver ions.

With the above, in the ion exchange fiber, silver ions capable of killing living germs through contact therewith is bonded, through e.g. an ion exchange reaction, with some or all of exchange groups of a cation exchange fiber such as exchange groups (—$SO_3H$) of strong acid cation exchange fiber or exchange groups (—COOH) of weak acid cation exchange fiber. Thus, this ion exchange fiber per se has the antimicrobial property. Then, it follows that the fiber substrate mixed with this ion exchange fiber too provides antimicrobial effect.

More specifically, the cation exchange fiber has a total exchange capacity of more than 2 meq/g. So that, if this fiber has its entire exchange groups bonded with silver ions, the amount of silver ions will be more than 21.5 wt % relative to the cation exchange fiber. Further, with an ion exchange fiber, the ion exchange groups are located on the filament surface, so that most of the silver ions are located on the cation exchange fiber with an inter-distance between adjacent silver ions being in the unit of angstroms. As a result, all living germs coming into contact with the ion exchange fiber may come into contact with the silver ions also.

In other words, as the entire surface of the ion exchange fiber is afforded with the antimicrobial property, this ion exchange fiber may provide strong antimicrobial effect.

Then, needless to say, if the filter substrate is formed entirely of the ion exchange fiber having such strong antimicrobial effect, it naturally follows that this filter will provide a very strong antimicrobial effect. Moreover, even if the filter substrate is formed of mixture of the ion exchange fiber and a further fiber (e.g. polyester fiber), provided that the ion exchange fiber is present in a predetermined amount with being uniformly dispersed throughout the filter substrate; then, this filter too can provide sufficient antimicrobial group to kill not only the germs entrapped within the substrate but also other germs tending to just pass through the substrate together with the air. Consequently, the air or gas passing through the filter substrate may be rendered into germ-free sterile condition.

As to the 'predetermined amount' described above, if the total amount of the silver ions which come to be present in the filter substrate by dispersing and mixing into the filter substrate the cation exchange fiber having some or all of the ion exchange groups or bonding groups thereof bonded with silver ions is equivalent to an amount of silver ions which would be present in the filter substrate if this substrate were mixed with more than 10 wt % of antimicrobial fiber having all exchange groups or bonding groups thereof exchanged or bonded with silver ion; then, this filter substrate is supposed to obtain such strong antimicrobial effect capable of killing also the germs passing through it with the air. This has been confirmed through an experiment to be described later.

Accordingly, with the first invention, it is possible to render the air or gas passing through the filter substrate into a sterile condition.

According to the second invention, said antimicrobial fiber comprises chelate fiber, and the total amount of the silver ions present in the chelate fiber is equivalent to an amount of silver ions contained in an antimicrobial fiber which is mixed at more than 10 wt % in the filter substrate and which has entire bonding groups thereof bonded with silver ions.

With the above, the chelate fiber has some or all of bonding groups thereof bonded with the silver ions capable of killing the germs through contact therewith, so that this chelate fiber per se provides the antimicrobial effect. Then, it naturally follows that the filter substrate mixed with this chelate fiber too provides the antimicrobial effect.

More specifically, chelate fiber has a metal ion bonding equivalent of more than 1.5 meq/g. Then, if the entire bonding groups of chelate fiber are bonded with silver ions, the amount of silver ions bonded within the chelate fiber will exceed 16.7 wt % relative to the chelate fiber. As a result, with this chelate fiber, most of the silver ions are present on the surface of the chelate fiber, with an inter-distance between the adjacent silver ions being in the unit of some angstroms, whereby all of the living germs coming into contact with the chelate fiber may come into contact with the silver ions also.

In other words, as the entire surface obtains the antimicrobial property, this chelate fiber may provide a very strong antimicrobial effect.

Then, needless to say, if the filter substrate is formed entirely of the chelate fiber having such strong antimicrobial effect, it naturally follows that this filter will provide a very strong antimicrobial effect. Moreover, even if the filter substrate is formed of mixture of the chelate fiber and a further fiber (e.g. polyester fiber), provided that the chelate fiber is present in a predetermined amount with being uniformly dispersed throughout the filter substrate; then, this filter too can provide sufficient antimicrobial group to kill not only the germs entrapped within the substrate but also other germs tending to just pass through the substrate together with the air. Consequently, the air or gas passing through the filter substrate may be rendered into germ-free sterile condition.

If the total amount of the silver ions which come to be present in the filter substrate by dispersing and mixing into the filter substrate the chelate fiber having some or all of the bonding groups thereof bonded with silver ions is equivalent to an amount of silver ions which would be present in the filter substrate if this substrate were mixed with more than 10 wt % of chelate fiber having all bonding groups thereof bonded with silver ions; then, this filter substrate is supposed to obtain such strong antimicrobial effect capable of killing also the germs passing through it with the air. This has been confirmed through the experiment to be described later.

Therefore, with the second invention too, the air or gas passing through the filter substrate may be reliably rendered into germ-free sterile condition.

Then, the above invention has provided a germ-removing filter capable of reliably effecting a germ-removing treatment by maintaining the gas passing therethrough at a sterile condition without living germs.

Preferably, the germ-removing filter has its face on the gas transmission side laminated with a gas-permeable film.

With the above, the gas transmission side face of the filter substrate comprised of non-woven fabric or paper fabric is laminated with a gas-permeable film comprised of e.g. a fluorine film in the thickness of 5 to 20 μm by such means as heat fusing adhesion, whereby the entrapping effect for living germs may be further enhanced.

As a result, there has been achieved a germ-removing filter having the further improved germ entrapping rate and germ-removing performance.

An apparatus for maintaining a sterile room under a sterile condition, according to the present invention, comprises the germ-removing filter according to the first or second invention incorporated with an air supply passage or air exhaust passage extending to the sterile room so as to filter the gas flowing therethrough.

With the above, it is possible to reliably prevent invasion of living germs into the sterile room through the air supply passage or the air exhaust passage by means of the germ-removing filter incorporated therein.

As a result, the invention has achieved an apparatus for maintaining a sterile room under a sterile condition which apparatus may reliably prevent invasion of living germs into the sterile room through the air supply passage or the air exhaust passage extending thereto.

According to a further aspect of the present invention, an apparatus for maintaining a sterile room under a sterile condition comprises a HEPA filter incorporated within an air supply passage extending to the sterile room so as to filter the gas flowing therethrough; and the germ-removing filter according to the first or second invention disposed upstream of or inside the HEPA filter.

With the above, the HEPA filter (high-performance filter) is incorporated within the air supply passage so as to filter the air to be supplied into the sterile room. Thus, fine particles present in the supplied air may be entrapped, so that the sterile room may be maintained under highly clean condition.

Moreover, it is also possible to maintain a germ-free sterile condition at the area downstream of the HEPA filter inside the air supply passage extending to the sterile room including the HEPA filter per se. In this case, the HEPA filter may still be subjected to proliferation of germs due to e.g. humidity variation. Yet, in case the germ-removing filter is disposed upstream of this HEPA filter, the entire HEPA filter may be maintained under a germ-free sterile condition. Or, in case the germ-removing filter is disposed inside the HEPA filter, the portion of the HEPA filter downstream of the germ-removing filter may be maintained under a germ-free sterile condition, so that the germ proliferation may be reliably prevented at this area. Consequently, the gas passing through the HEPA filter may be maintained under the germ-free sterile condition, whereby germ-free gas may be supplied to the sterile room. In other words, if the germ-removing filter were alternatively disposed downstream of the HEPA filter, in this case too the gas to be supplied into the sterile room could be rendered germ-free. However, with this arrangement, there would occur the possibility of germ proliferation in the HEPA filter. Then, with such germ proliferation in the HEPA filter, the germ-removing filter would have to remove much greater number of living germs, for which purpose a greater performance would be required of this germ-removing filter, whereby e.g. cost increase would result. On the other hand, according to the above-proposed arrangement of the present invention, there occurs no such inconvenience since the germ proliferation in the HEPA filter may be reliably prevented or restricted.

Consequently, there has been achieved an apparatus for maintaining a sterile room under a sterile condition, which apparatus may reliable prevent invasion of living germs and fine particles into the sterile room through the air supply passage extending to the sterile room.

Further and other objects, features and effects of the invention will become more apparent from the following more detailed description of the embodiments of the invention with reference to the accompanying drawings.

DETAILED DESCRIPTION OF THE PREFERRED EMBODIMENTS

Preferred embodiments of a germ-removing filter and an apparatus for maintaining a sterile room under a sterile condition both according to the present invention will be described in detail with reference to the accompanying drawings.

Embodiments 1 through 3 relate to the basic constructions of the invention, while Embodiment 4 relates to a more specific construction.

Embodiment 1

Figure 1:
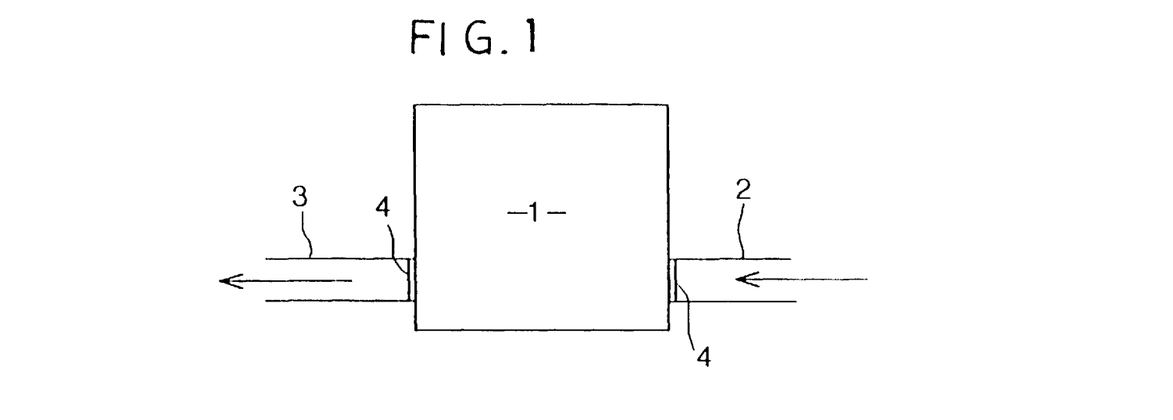
FIG. 1 is a schematic construction view showing a first embodiment of the invention.

FIG. 1 shows an apparatus for maintaining -a sterile room (bioclean room) under a sterile condition. More specifically, a germ-removing filter 4 is disposed respectively within an air supply passage 2 and an air exhaust passage 3 extending and communicating to the sterile room 1 so as to filter the air or gas passing therethrouah for preventing invasion of living germs into the sterile room 1 via the air supply passage 2 and air exhaust passage 3.

The germ-removing filter 4 is disposed at an air discharge opening of the air supply passage 2 opened to the sterile room 1. The further germ-removing filter 4 is disposed at an exhaust air intake opening of the air exhaust passage 3 opened to the sterile room 1.

Embodiment 2

Figure 2:
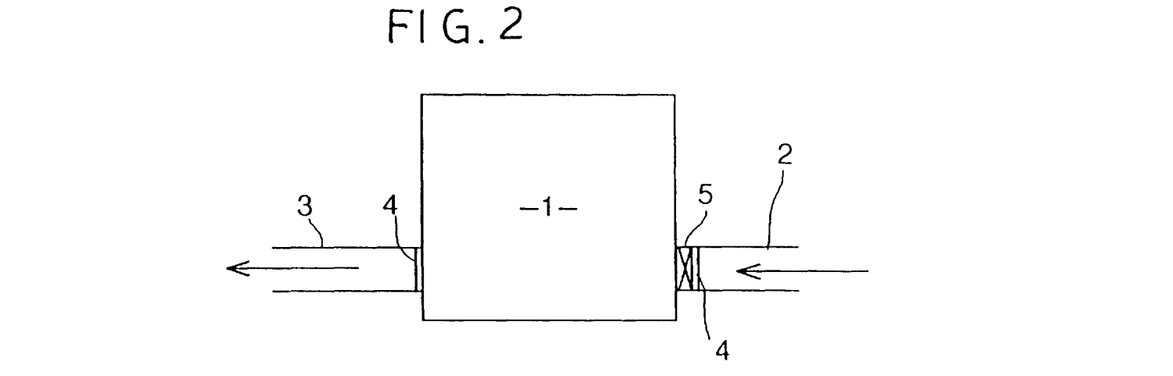
FIG. 2 is a schematic construction view showing a second embodiment of the invention.

FIG. 2 shows an apparatus, according to this further embodiment, for maintaining a sterile room (bioclean room) under a sterile condition.

More specifically, a HEPA filter 5 for filtering air is disposed within an air supply passage 2 extending to a sterile room 1, with the HEPA filter 5 forming an air discharge opening into the sterile room 1. Further, a germ-removing filter 4 is disposed at an entrance of the HEPA filter 5, so as to supply the dust-removed and germ-removed air into the sterile room 1. Also, like the Embodiment 1, another germ-removing filter 4 is disposed within an air exhaust passage 3 from the sterile room 1, so as to prevent invasion of living germs into the sterile room 1 via the air exhaust passage 3. Needless to say, invasion of living germs into the sterile room 1 via the air supply passage 2 is prevented by the above-mentioned germ-removing filter 4 incorporated within the air supply passage 2.

Embodiment 3

Figure 3:
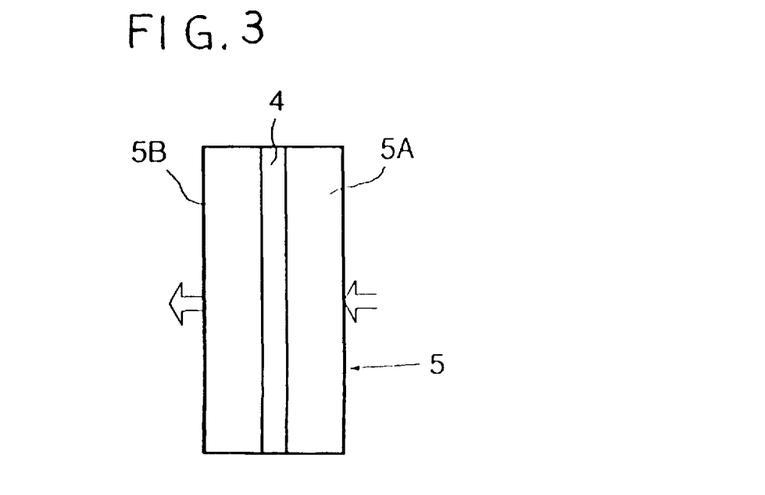
FIG. 3 is a schematic construction view showing principal portions of a third embodiment of the invention.

FIG. 3 shows a still further embodiment. In this embodiment, in the construction of Embodiment 2, the germ-removing filter 4 is disposed inside the HEPA filter 5, instead of upstream of the same. More particularly, in this further construction, the germ-removing filter 4 is interposed between an upstream filter member 5A and a downstream filter member 5B of the HEPA filter, so as to constitute together a multi-layered filter assembly.

Incidentally, the air supply system to the sterile room 1 in the above Embodiments 1 through 3, may be either a recirculating type for cleaning exhaust air from the sterile room 1 and recycling this cleaned air into the sterile room 1 again or a one-passage type for constantly feeding fresh air into the sterile room 1.

Embodiment 4

Figure 4:
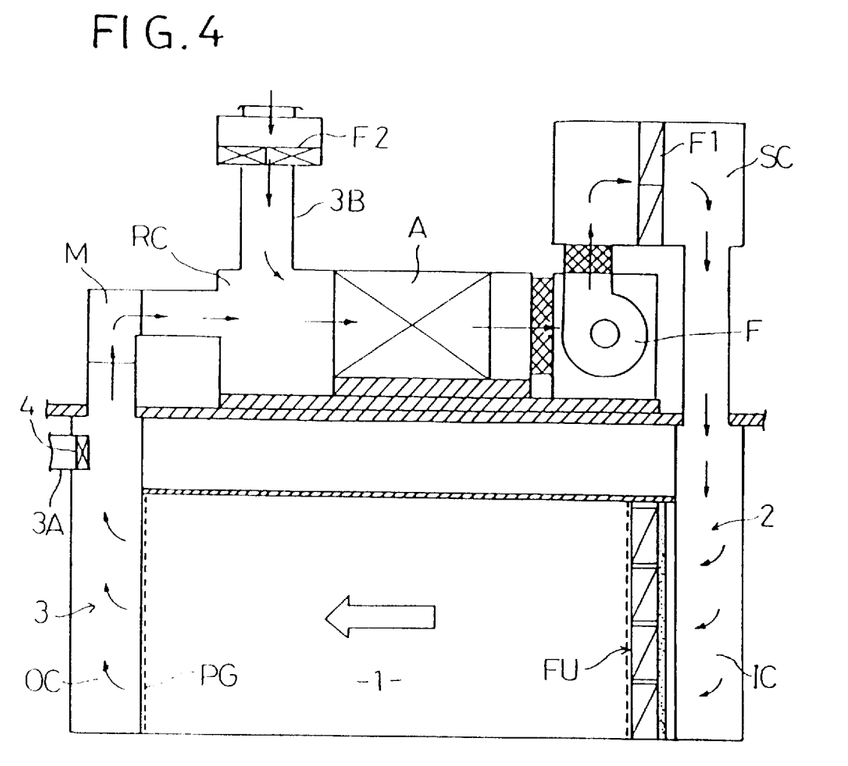
FIG. 4 is a schematic construction view showing a sterile clean room and an air conditioning system therefor relating to a fourth embodiment of the invention.

Next, an application of the invention to a germ-free clean room 1 will be described. As shown in FIG. 4, an air-conditioning system (including the sterility maintaining apparatus) for this germ-free clean room comprises the recirculating type. One of opposed walls of the germ-free clean room 1 is constituted from a filter unit FU forming an air discharge opening of an air supply passage 2 opened into the clean room 1. The other wall is constituted from a punching grill PG forming an exhaust air intake opening of an air exhaust passage 3 from the clean room 1. In an upper region of the clean room 1, there is provided an air-conditioner A for conditioning the temperature and humidity of the air. The conditioned air from this air-conditioner A is pressure-fed into the clean room 1 via the air supply passage 2. Further, there is provided a blower F, such that the air inside the germ-free clean room 1 is sucked into the air exhaust passage 3 and recycled to the air-conditioner A, whereby the air is recycled between the air-conditioner A and the germ-free clean room 1. The air supply passage 2 incorporates therein an aerosol filter F1. The air exhaust passage 3 is connected with an exhaust passage 3A for exhausting a portion of the exhaust air, i.e. the air to be returned to the blower F to the outside of the system and an ambient air introducing passage 3B for introducing fresh air (i.e. ambient air) into the air exhaust passage 3. And, this ambient air introducing passage 3B incorporates therein a roll filter F2, and a germ-removing filter 4 of low pressure-loss type is attached to an entrance of the exhaust passage 3A, respectively.

In operation, with an activation of the blower F with the air-conditioner A in operation, the air conditioned by the air-conditioner A is filtered through the aerosol filter F1 and then filtered through the filter unit FU to be supplied into the germ-free clean room 1. Then, the air inside the clean room 1 is sucked through the punching grill PG and a portion of this air is exhausted via the exhaust passage 3A to the outside of the system and fresh ambient air is introduced in place thereof via the ambient air introducing passage 3B, so that the exhaust air a portion of which has been replaced by the fresh air is recycled to the air-conditioner A.

Figure 5:
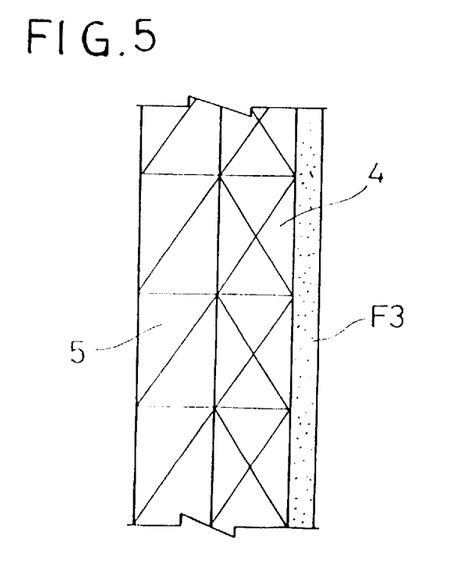
FIG. 5 is an enlarged schematic section view showing principal portions of the fourth embodiment.

As shown in FIG. 5, the filter unit FU comprises a multi-layered filter assembly including a pre-filter F3, the germ-removing filter 4 and the HEPA filter 5 disposed in series in the mentioned order from the upstream side. That is, with this filter unit FU, the air passing therethrough may be rendered germ-free and dust-removed. As a result, this germ-free and dust-removed air may be supplied into the clean room 1.

Of the air supply passage 2, a portion thereof incorporating the aerosol filter F1 is constituted from a supply chamber SC for rendering the air from the blower F into static-pressure, rectified air to be supplied to the aerosol filter F1 and then again rendering the air through this aerosol filter F1 into static-pressure, rectified air flow. A portion of the air supply passage 2 for supplying air to the filter unit FU is constituted from a chamber IC having a capacity sufficient to supply air to the entire surface of the filter unit FU and capable of rending the air into static-pressure, rectified air to be supplied to the filter unit FU.

On the other hand, of the air exhaust passage 3 acting as the return passage from the clean room 1 to the air-conditioner A, a portion thereof for sucking the air through the punching grill PG is constructed as a chamber OC having a capacity sufficient to suck air from the entire surface of the punching grill PG, and a further portion thereof for mixing the introduced fresh air into the recycled air to be supplied to the air-conditioner A is constructed as a return chamber RC for rendering the mixed air into static-pressure, rectified air flow to be guided to the air-conditioner A. Further, this air exhaust passage 3 includes a silencer elbow M for restricting operation noises of the blower F and/or the air-conditioner A from being transmitted via the air exhaust passage 3 to reach the germ-free clean room 1.

Next, the germ-filters 4 employed in the above Embodiments 1 through 4 will be described in details.

Each of these germ-removing filters 4 comprises e.g. a gas-permeable filter substrate mixed and dispersed with antimicrobial fiber, or gas-permeable filter substrate mixed and dispersed with antimicrobial fiber and having a gas transmission side face thereof laminated with a gas transmission film.

The filter substrate actually is a non-woven fabric having a METSUKE amount ranging 40–200 $g/m^2$, which comprises a mixture fiber of a primary substrate fiber and the antimicrobial fiber.

The primary substrate fiber can be e.g. a polyester type synthetic fiber, typically polyethylene terephthalate (PET).

The antimicrobial fiber can be e.g. ion exchange fiber, or chelate fiber.

More particularly, the ion exchange fiber can be an ion exchange fiber in which silver ions are bonded through an ion exchange reaction with some or all of exchange groups (—$SO_3H$) of a strong acid cation exchange fiber, i.e. an ion exchange fiber including $SO_3Ag$, or a further ion exchange fiber in which silver ions are bonded through an ion exchange reaction with some or all of exchange groups (—COOH) of a weak acid cation exchange fiber, i.e. an ion exchange fiber having —COOAg.

The chelate fiber can be e.g. a chelate fiber in which silver ions are bonded with some or all of bonding groups of the chelate fiber, i.e. a chelate fiber having some or all of chelate ligands thereof bonded with silver ions. One specific example thereof is PVA fiber added and crosslinked with PEI (polyethylene imines) and expressed by the following chemical expression;

Through contact with living germs, the ion exchange fibers and chelate fibers described above provide an antimicrobial effect thereon due to the antimicrobial property of the silver ions bonded with the fiber. That is, germ proliferation prevention and sterilization are effected on the surface of the fibers by the antimicrobial effect of the silver ions located on the fiber surface.

Next, the ion exchange fiber and the chelate fiber will be described in greater details.

If a cation exchange fiber having a total ion exchange capacity of more than 2 meq/g is chosen; then, if silver ions are bonded with all of the exchange groups thereof, the total amount of the silver ions contained in this ion exchange fiber will be more than 21.5 wt % relative to the cation exchange fiber. As a result, most the silver ions are located on the surface of the cation exchange fiber with an inter-distance between the adjacently located silver ions being in the order of some angstrome (A) units, whereby all living germs coming into contact with the surface of this ion exchange fiber will come into contact with the silver ions also. On the other hand, if a chelate fiber having a bonding equivalent of more than 1.5 meq/g is chosen; then, if silver ions are bonded with all of the bonding groups thereof, the total amount of the silver ions contained within this chelate fiber will be more than 16.7 wt % relative to the chelate fiber. As a result, most the silver ions are located on the surface of the chelate fiber with an inter-distance between the adjacently located silver ions being in the order of some angtrome. (A) units, whereby all living germs coming into contact with the surface of this chelate fiber will come into contact with the silver ions also.

Next, there will be described some specific means for bonding silver ions with the cation exchange fiber to produce an ion exchange fiber.

<1> Before being mixed with the primary substrate fiber, the cation exchange fiber is caused to be bonded with silver ions. That is, when the filter is produced by mixing, this filter has already obtained the antimicrobial property as being the mixture of the antimicrobial ion exchanger fiber and the primary substrate fiber.

<2> First, the cation exchange fiber and the primary substrate fiber are mixed together to produce a non-antimicrobial filter substrate. Then, this non-antimicrobial filter substrate is caused to be bonded with silver ions, whereby a filter is produced with the silver ions being present in the dispersed state within the ion exchange fiber thereof.

Next, there will be described some specific means for bonding silver ions with the chelate fiber to produce a chelate fiber filter material.

<3> Before being mixed with the primary substrate fiber, the chelate fiber is caused to be bonded with silver ions. That is, when the filter material is produced by mixing, this filter material has already obtained the antimicrobial property as being the mixture of the antimicrobial chelate fiber and the primary substrate fiber.

<4> First, the chelate fiber and the primary substrate fiber are mixed together to produce a non-antimicrobial filter substrate. Then, this non-antimicrobial filter substrate is caused to be bonded with silver ions, whereby a filter material is produced with the silver ions being present in the dispersed state within the chelate fiber thereof.

Next, some specific methods of producing the ion exchange fiber by the above means <1> and <2> will be described.

<1> Strong acid cation exchange fiber having a total exchange capacity of 2.2 meq/g is submerged and stirred for 20–30 minutes in 1.0 wt % silver nitrate solution (40 liters in case the strong cation exchange fiber is 1 kg) so that 400 g of silver nitrate is present for 1 kg of the strong acid cation exchange fiber having the 2.2 meq/g total ion exchange capacity. Thereafter, the solution is dehydrated by a centrifugal dehydrator. Then, the obtained strong acid cation exchange fiber is rinsed with pure water and then this fiber is subjected again to a centrifugal dehydration. Thereafter, the fiber is dried naturally in the air or by using a drier until the water content of the fiber becomes lower than 10 wt %. The resultant fiber is then cut into a length (about 25–30 mm) required for making non-woven fabric. Incidentally, the water rinsing operation of the strong cation exchange fiber with pure water is effected until hydrochloric acid dripped into the rinsing water no longer produces nebula of silver nitrate.

<2> Strong acid cation exchange fiber having a total ion exchange capacity of 2.2 meq/g is cut into a length (about 25–30 mm) required for making a nonwoven fabric. Then, this cut strong acid cation exchange fiber is packed into a packed column so that the packed fiber obtains a density of about 0.2–0.3 g/cc. Silver nitrate solution of 0.5–2.0 wt % is introduced into the packed column (i.e. the packed strong acid cation exchange fiber) at the rate of SV= 3–10/Hr (hour) so that 400 g of silver nitrate is present per 1 Kg of packed strong acid cation exchange fiber. Thereafter, the fiber is rinsed with pure water until hydrochloric acid dripped into the rinsing water no longer produces nebula of silver nitrate. Then, the obtained ion exchange fiber is removed from the column and then subjected to a centrifugal dehydration. The resultant fiber is dried naturally in the air or by using a drier until the fiber obtains a water content of less than 10 wt %.

Next, some specific methods of producing the chelate fiber by the above means <3> and <4> will be described.

<3> chelate fiber having a metal ion bonding equivalent of 1.6 meq/g is submerged and stirred for 20–30 minutes in 1.0 wt % silver nitrate solution so that about 270 g of silver nitrate is present for 1 kg of the chelate fiber having the 1.6 meq/g metal bonding equivalent. Thereafter, the solution is dehydrated by a centrifugal dehydrator. Then, the obtained chelate fiber is rinsed with pure water and then this fiber is subjected again to a centrifugal dehydration. Thereafter, the fiber is dried naturally in the air or by using a drier until the water content of the fiber becomes lower than 10 wt %. The resultant fiber is then cut into a length (about 25–30 mm) required for making non-woven fabric. Incidentally, the water rinsing operation of the chelate fiber with pure water is effected until hydrochloric acid dripped into the rinsing water no longer produces nebula of silver nitrate.

<4> Chelate fiber having a metal ion bonding equivalent of 1.6 meq/g is cut into a length (about 25–30 mm) required for making a non-woven fabric. Then, this cut chelate fiber is packed into a packed column so that the packed fiber obtains a density of about 0.2–0.3 g/cc. Silver nitrate solution of 0.5–2.0 wt % is introduced into the packed column (i.e. the packed chelate fiber) at the rate of SV=3–10/Hr (hour) so that about 270 g of silver nitrate is present per 1 Kg of packed chelate exchange fiber. Thereafter, the fiber is rinsed with pure water until hydrochloric acid dripped into the rinsing water no longer produces nebula of silver nitrate. Then, the obtained chelate fiber is removed from the column and then subjected to a centrifugal dehydration. The resultant fiber is dried naturally in the air or by using a drier until the fiber obtains a water content of less than 10 wt %.

Followings are some specific methods for making the fiber substrate from the ion exchange fiber obtained by the method <1>.

(a) For making the ion exchange fiber into a fiber substrate, binder fiber is added to the ion exchange fiber in a mixture ratio to be detailed later, and by the dry method, this mixture fiber is processed into a filter substrate as a non-woven fabric.

(b) By the wet method, the fiber substrate may be produced as non-woven fabric. Or by the paper making method, the fiber substrate may be produced as paper fabric.

Incidentally, in case the fiber substrate is produced as non-woven fabric by using the wet method or into paper fabric by using the paper making method, the binder will be added without the drying step. And, in these manufacture processes, pure water is used as paper making water.

Followings are some specific methods for producing fiber substrate from the chelate fiber obtained by the method <3>.

(c) For making the chelate fiber into a fiber substrate, binder fiber is added to the chelate fiber in a mixture ratio to be detailed later, and by the dry method, this mixture fiber is dried to produce a filter substrate as a non-woven fabric.

(d) By the wet method, the fiber substrate may be produced as non-woven fabric (e). Or by the paper making method, the fiber substrate may be produced as paper fabric.

Incidentally, in these cases, the binder will be added without the drying step. And, in these manufacture processes, pure water is used as paper making water.

As described above, both the ion exchange fiber and the chelate fiber may be made into fiber substrate by the identical methods.

Next, a sample method of making the ion exchange fiber by the method <2>, i.e. a making method for antimicrobial fiber substrate will be described.

By the dry method or wet method and based on a mixture fiber with polyethylene terephthalate fiber containing strong acid cation exchange fiber having a total ion exchange capacity of 2.2 meq/g in a predetermined ratio (e.g. 10 wt % or 30 wt % or 50 wt %), non-woven fabric (non-antimicrobial filter substrate) having a thickness of about 10 mm and a METSUKE amount of 190–200 g/m² is produced.

After this non-woven fabric is submerged about 20 minutes in 0.5 wt % silver nitrate solution at an amount according to the content of the strong acid cation exchange fiber, the fabric is dehydrated by a centrifugal dehydrator. After this dehydration, the fabric is rinsed with pure water and then dried naturally in the air or by using a drier. Incidentally, the water rinsing operation of the non-woven fabric with pure water is carried out until hydrochloric acid dripped into the rinsing water no longer produces nebula of silver nitrate.

Next, a sample method of making the chelate fiber by the method <4>, i.e. a making method for antimicrobial fiber substrate will be described.

By the wet method for a mixture fiber with polyethylene terephthalate fiber containing chelate fiber having a bonding equivalent of 1.6 meq/g in a predetermined ratio (e.g. 10 wt % or 30 wt % or 50 wt %), non-woven fabric (non-antimicrobial filter substrate) having a thickness of about 10 mm and a METSUKE amount of 190–200 g/m² is produced.

After this non-woven fabric is submerged about 20 minutes in 0.5 wt % silver nitrate solution at an amount according to the content of the chelate fiber, the fabric is dehydrated by a centrifugal dehydrator. After this dehydration, the fabric is rinsed with pure water and then dried naturally in the air or by using a drier. Incidentally, the water rinsing operation of the non-woven fabric with pure water is carried out until hydrochloric acid dripped into the rinsing water no longer produces nebula of silver nitrate.

Next, the mixing amount of the antimicrobial fiber for making the fiber substrate from the mixture fiber will be detailed.

In case ion exchange fiber is employed as the antimicrobial fiber, this ion exchange fiber is mixed into the fiber substrate so that the total amount of the silver ions contained in the filter substrate through its mixing with the ion exchange fiber is equivalent to an amount of silver ions which would be present in a filter substrate mixed with more than 10 wt % of an ion exchange fiber having all of exchange groups thereof bonded with silver ions. That is to say, if the employed ion exchange fiber has not all of but only some of ion exchange groups thereof bonded with silver ions; then, the mixing amount of this ion exchange fiber will be set greater than a mixing amount of the further ion exchange fiber having all of the ion exchange groups thereof bonded with silver ions, thereby to compensate for the shortage of silver ions. More specifically, if the employed ion exchange fiber has only half of the ion exchange groups thereof bonded with silver ions; then, the total amount of the silver ions will be half of that present in the further ion exchange fiber having all of the ion exchange groups thereof bonded with silver ions. In this case, therefore, in comparison with the case using the further ion exchange fiber having all of its ion exchange groups bonded with silver ions, the mixing amount of the ion exchange fiber will be doubled, so as to compensate for the amount of the silver ions contained in the filter substrate.

Similarly, in case chelate fiber is employed as the antimicrobial fiber, this chelate fiber is mixed into the fiber substrate so that the total amount of the silver ions contained in the filter substrate through its mixing with the ion exchange fiber is equivalent to an amount of silver ions which would be present in a filter substrate mixed with more than 10 wt % of a chelate fiber having all of bonding groups thereof bonded with silver ions. That is to say, if the employed chelate fiber has not all of but only some or chelate groups thereof bonded with silver ions; then, the mixing amount of this chelate fiber will be set greater than a mixing amount of the further chelate fiber having all of the bonding groups thereof bonded with silver ions, thereby to compensate for the shortage of silver ions. More specifically, if the employed chelate fiber has only half of the bonding groups thereof bonded with silver ions; then, the total amount of the silver ions will be half of that present in the further chelate fiber having all of the bonding groups thereof bonded with silver ions. In this case, therefore, in comparison with the case using the further chelate fiber having all of its chelate groups bonded with silver ions, the mixing amount of the chelate fiber will be doubled, so as to compensate for the amount of the silver ions contained in the filter substrate.

The filter substrate having the antimicrobial fiber mixed and dispersed therein obtains an antimicrobial effect, as has been demonstrated by the experiment to be described later.

Table 1 belows shows some specific examples of contents of the strong acid cation exchange fiber and chelate fiber in the filter substrate and the amounts of 0.5 wt % silver nitrate solution to be used in accordance with the above fiber contents, so as to produce antimicrobial fibers from these strong acid cation exchange fiber and chelate fiber.

TABLE 1

| | type | | | |
|---|---|---|---|---|
| | cation exchange fiber mixed non-woven fabric | | chelate fiber mixed non-woven fabric | |
| content | total exchange capacity (meq/g) | liquid total amount (litter) | bonding equivalent (meq/g) | liquid amount (litter) |
| 10 | 22 | 1.5 | 18 | 1.1 |
| 30 | 66 | 4.5 | 54 | 3.3 |
| 50 | 110 | 7.5 | 90 | 5.5 |

Some specific methods of the laminating are: heat fusing adhesion of a fluorine type gas-permeable film having a thickness of 5–10 $\mu$m to one side face of the filter substrate; and heat-fusing of a fluorine type gas-permeable film having a thickness of 5–10 $\mu$m to the one side face of the filter substrate by using a low melting point (e.g. 290° C.) polyester resin as a fusing agent. One specific example of the fluorine type gas-permeable film is polytetrafuloroethylene (PTFE).

The laminating treatment of the filter substrate can improve the germ-removing performance of the filter substrate.

Next, there will be described the experiment conducted by the present inventors in order to confirm the antimicrobial effect of the filter substrate having the antimicrobial fiber mixed and dispersed therein, i.e. the antimicrobial effect of the germ-removing filter of the present invention.

Experiment 1

Figure 6:
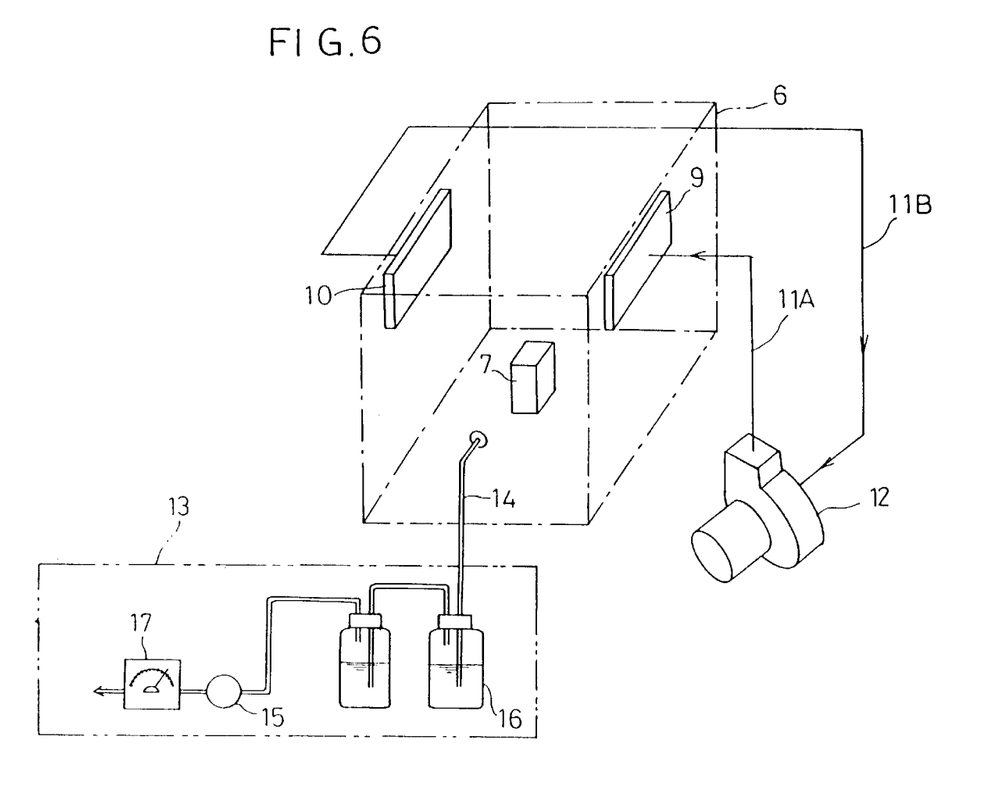
FIG. 6 is a schematic construction view showing an experiment system.

First, an experiment system used in the determination of the antimicrobial properties will be described. This experiment system, as shown in FIG. 6, includes a booth 6 usable in testing of an air-purifying filter. The booth 6, which is formed of acrylic material, has dimensions of 100 cm×100 cm×100 cm. Inside this booth 6, there is disposed an ultrasonic nebulizer as an example of a micro-organism particle generator. In opposed side faces of the booth 6, there are defined a filter attaching opening 9 and a recirculating opening 10, respectively. The system further includes an air circulating fan 12 (0.75m³/min), so that air is fed via a duct 11A through the filter attaching opening 9 into the booth 6, while the air present inside the booth 6 is sucked via a duct 71B through the air recirculating opening 10 to be recirculated. An ail sampler 13 is provided for sampling the air inside the booth 6. This air sampler 13 includes a sampling tube 14 for sucking the air from the inside of the booth 6, a suction fan 15 for sucking the air from the booth 6, a collecting vial 16 for collecting micro-organisms present in the sucked air, and an air flow meter 17 for metering the amount of the sucked air.

Next, the method of this experiment will be described.

As a suspension liquid of micro-organisms, *Escherichia coli* was uniformly dispersed in sterilized water to obtain suspension liquid of $1.7 \times 10^8$ CFU/ml. Further, as samples, as shown in Table 2, there were prepared various kinds of non-woven fabrics (A1) through (A8) comprising mixture fiber of polyethylene terephthalate fiber containing strong acid cation exchange fiber having a total ion exchange capacity of 2.2 meq/g and having all of the ion exchange groups thereof bonded with silver ions, in a variety of mixing ratios (1.0 wt %, 10 wt %, 30 wt %, 50 wt %); and further non-woven fabrics (A9), (A10) produced respectively by laminating fluorine type gas-permeable film to the two kinds of non-woven fabrics (A1) and A2) described above. Further, as shown in Table 3, there were also prepared various kinds of non-woven fabrics (B1) through (B8) including mixture fiber of polyethylene terephthalate fiber containing chelate fiber having a bonding equivalent of 1.6 meq/g and having all of the bonding groups thereof bonded with silver ions, in a variety of mixing ratios (1.0 wt %, 10 wt %, 30 wt %, 50 wt %); and further non-woven fabrics (B9), (B10) produced respectively by laminating fluorine type gas-permeable film to the two kinds of non-woven fabrics (B1) and (B2) described above.

Then, the above-described samples were attached to the filter attaching opening 9 of the booth 6 and the ultrasonic nebulizer T was operated to atomize the micro-organism suspension liquid at the rate of 5 ml/5 min to spray the atomized micro-organism suspension liquid into the booth 6, and then the air circulating fan 12 was activated. After 15 minutes, 30 minutes and 60 minutes of the operation of the air circulating fan 12, respectively, the air in the booth 6 is sucked by the air sampler 13 at the rate of 1 litter/min for 10 minutes to collect micro-organisms.

Then, these samples having entrapped the micro-organisms were maintained respectively for 12 hours inside a desiccator set at a relative humidity of 60%. Thereafter, these samples were rinsed with physiological salt solution and then incubated for 24 hours at 37° C. using BL culture medium. Then, the numbers of germs were counted. Incidentally, germs were collected also from blank samples those without attachment of the filters.

The results of the measurements are shown in Tables 2 and 3.

As may be seen from the results of the above experiment, the filter substrate, if containing antimicrobial fiber such as ion exchange fiber or chelate fiber at more than 10 wt %, may provide sufficient antimicrobial effect.

Further Embodiments

In the foregoing embodiment, the antimicrobial filter substrate is formed from the mixture fiber of a primary fiber substrate such as polyester type synthetic resin and the antimicrobial fiber. Instead, the entire fiber substrate may be formed of the antimicrobial fiber.

In the foregoing embodiment, the germ-removing filter 4 is disclosed in the form of non-woven fabrics. Instead, the germ-removing filter 4 may be provided as knitted fabric, paper or the like.

The invention may be embodied in other specific forms without departing from the spirit or essential characteristics thereof. The present embodiments are therefore to be considered in all respects as illustrative and not restrictive, the scope of the invention being indicated by the appended claims rather than the foregoing description and all changes which come within the meaning and range of equivalency of the claims are therefore intended to be embraced therein.

TABLE 2 cation exchange fiber substrate

| sample | fan operating time (min.) | air amount past filter/booth capacity | anti-microbial number of germs (CFU/ml) | compared items filter material specifications | | |
|---|---|---|---|---|---|---|
| | | | | fiber content (%) | thickness (mm) | METSUKE amount (g/m$^2$) |
| A-1 | 15 | 10 | $1.0 \times 10^4$ | 1% | 1 | 180–190 |
| | 30 | 20 | $2.5 \times 10^3$ | | | |
| | 60 | 40 | $1.2 \times 10^2$ | | | |
| A-2 | 15 | 10 | $4.9 \times 10^4$ | 10% | 1 | 180–190 |
| | 30 | 20 | $1.5 \times 10^2$ | | | |
| | 60 | 40 | not detected | | | |
| A-3 | 15 | 10 | $2.5 \times 10^3$ | 30% | 1 | 180–190 |
| | 30 | 20 | $3.0 \times 10^2$ | | | |
| | 60 | 40 | not detected | | | |
| A-4 | 15 | 10 | $1.5 \times 10^2$ | 50% | 1 | 180–190 |
| | 30 | 20 | not detected | | | |
| | 60 | 40 | not detected | | | |
| A-5 | 15 | 10 | $4.5 \times 10^4$ | 1% | 0.5 | 90–100 |
| | 30 | 20 | $1.8 \times 10^4$ | | | |
| | 60 | 40 | $1.0 \times 10^2$ | | | |
| A-6 | 15 | 10 | $2.0 \times 10^4$ | 10% | 0.5 | 90–100 |
| | 30 | 20 | $6.5 \times 10^2$ | | | |
| | 60 | 40 | not detected | | | |
| A-7 | 15 | 10 | $7.5 \times 10^2$ | 30% | 0.5 | 90–100 |
| | 30 | 20 | not detected | | | |
| | 60 | 40 | not detected | | | |
| A-8 | 15 | 10 | 12 | 50% | 0.5 | 90–100 |
| | 30 | 20 | not detected | | | |
| | 60 | 40 | not detected | | | |
| A-9 | 15 | 10 | $1.2 \times 10^2$ | 1% laminated | 1 | 180–190 |
| | 30 | 20 | 6 | | | |
| | 60 | 40 | not detected | | | |
| A-10 | 15 | 10 | $1.0 \times 10^2$ | 10% laminated | 1 | 180–190 |
| | 30 | 20 | not detected | | | |
| | 60 | 40 | not detected | | | |
| blank | 15 | 10 | $9.2 \times 10^4$ | | | |

TABLE 3 chelate fiber filter substrate

| sample | fan operating time (min.) | air amount past filter/booth capacity | anti-microbial number of germs (CFU/ml) | compared items filter material specifications | | |
|---|---|---|---|---|---|---|
| | | | | fiber content (%) | thickness (mm) | METSUKE amount (g/m$^2$) |
| B-1 | 15 | 10 | $1.2 \times 10^4$ | 1% | 1 | 180–190 |
| | 30 | 20 | $1.8 \times 10^3$ | | | |
| | 60 | 40 | $2.5 \times 10^2$ | | | |
| B-2 | 15 | 10 | $2.4 \times 10^4$ | 10% | 1 | 180–190 |
| | 30 | 20 | $2.0 \times 10^2$ | | | |
| | 60 | 40 | not detected | | | |
| B-3 | 15 | 10 | $1.5 \times 10^3$ | 30% | 1 | 180–190 |
| | 30 | 20 | $1.9 \times 10^2$ | | | |
| | 60 | 40 | not detected | | | |
| B-4 | 15 | 10 | $2.4 \times 10^2$ | 50% | 1 | 180–190 |
| | 30 | 20 | not detected | | | |
| | 60 | 40 | not detected | | | |
| B-5 | 15 | 10 | $1.5 \times 10^5$ | 1% | 0.5 | 90–100 |
| | 30 | 20 | $2.4 \times 10^4$ | | | |
| | 60 | 40 | $1.3 \times 10^2$ | | | |
| B-6 | 15 | 10 | $5.4 \times 10^4$ | 10% | 0.5 | 90–100 |
| | 30 | 20 | $2.3 \times 10^2$ | | | |
| | 60 | 40 | not detected | | | |
| B-7 | 15 | 10 | $4.2 \times 10^2$ | 30% | 0.5 | 90–100 |
| | 30 | 20 | not detected | | | |
| | 60 | 40 | not detected | | | |
| B-8 | 15 | 10 | 20 | 50% | 0.5 | 90–100 |
| | 30 | 20 | not detected | | | |
| | 60 | 40 | not detected | | | |
| B-9 | 15 | 10 | $1.6 \times 10^2$ | 1% laminated | 1 | 180–190 |
| | 30 | 20 | 5 | | | |
| | 60 | 40 | not detected | | | |
| B-10 | 15 | 10 | $1.0 \times 10^2$ | 10% laminated | 1 | 180–190 |
| | 30 | 20 | not detected | | | |
| | 60 | 40 | not detected | | | |
| blank | 15 | 10 | $1.2 \times 10^5$ | | | |

What is claimed is:

1. A germ-removing filter, comprising:
   a filter substrate; and
   an antimicrobial material dispersedly mixed into the filter substrate, the antimicrobial material comprising antimicrobial fiber bonded with silver ions,
   wherein the antimicrobial fiber comprises cation exchange fiber having at least some of the cation-exchange groups thereof bonded with the silver ions through an ion exchange reaction,
   wherein the cation exchange fiber has a total exchange capacity of at least 21.5 wt % relative to the cation exchange fiber,
   wherein the total amount of the silver ions present in the filter is equivalent to the amount of silver ions present when the substrate contains at least 10 wt % of the antimicrobial fibers having all exchange groups exchanged with silver ions, and
   wherein a face of said filter substrate on an upstream side in a direction of gas permeation is laminated with a gas-permeable resin film.

2. A germ-removing filter as defined in claim 1, wherein said ion exchange fiber includes at least one of —SO$_3$Ag and —COOAg.

3. A germ-removing filter as claimed in claim 1, wherein the gas-permeable resin film comprises a fluorine containing film.

4. A germ-removing filter, comprising:
   a filter substrate; and
   an antimicrobial material dispersedly mixed into the filter substrate, the antimicrobial material comprising chelate fiber bonded with silver ions,
   wherein the antimicrobial fiber comprises chelate fiber having at least some of the bonding groups thereof bonded with the silver ions through a chelating reaction,
   wherein the chelate fiber has a total bonding capacity of at least 16.7 wt % relative to the chelate fiber,
   wherein the total amount of the silver ions present in the filter is equivalent to the amount of silver ions present when the substrate contains sit least 10 wt % of the antimicrobial fibers having all bonding groups bonded with silver ions, and
   wherein a face of said filter substrate on an upstream side in a direction of gas permeation is laminated with a gas-permeable resin film.

5. A germ-removing filter, comprising:

a filter substrate; and an antimicrobial material dispersedly mixed into the filter substrate, the antimicrobial material comprising antimicrobial fiber bonded with silver ions, wherein the antimicrobial fiber comprises chelate fiber having at least some of the bonding groups thereof bonded with silver ions through a chelating reaction, the chelating fiber being PVA fiber added and crosslinked with PEI (polyethylene imines) and expressed by the following chemical formula;

wherein the chelate fiber has a total bonding capacity of at least 16.7 wt % relative to the chelate fiber, wherein the total amount of the silver ions present in the filter is equivalent to the mount of silver ions present when the substrate contains at least 10 wt % of the antimicrobial fibers having all bonding groups bonded with silver ions, and wherein a face of the filter substrate on an upstream side in a direction of gas permeation is laminated with a gas-permeable film.

6. An apparatus for maintaining a sterile room under a sterile condition, which comprises:

a germ-removing filter comprising a filter substrate; and an antimicrobial material dispersedly mixed into the filter substrate, the antimicrobial material comprising antimicrobial fiber bonded with silver ions;

wherein the silver ions are bonded to the antimicrobial fiber through an ion exchange or chelating reaction wherein the total amount of the silver ions present in the filter is equivalent to the amount of silver, ion present when the substrate contains at least 10 wt % of the antimicrobial fibers having all exchange groups or bonding groups exchanged or bonded with silver ions, wherein the germ-removing filter is incorporated in at least one of an air supply passage and an air exhaust passage of the sterile room so as to filter the gas flowing therethrough, and wherein the filter substrate of said germ-removing filter has a gas transmission side with a face which is laminated with a gas-permeable film.

7. An apparatus as defined in claim 6 including an upstream pre-filter and a downstream HEPA filter, wherein said germ-removing filter is interposed between the upstream pre-filter and the downstream HEPA filter.

8. An apparatus as claimed in claim 6, wherein the gas-permeable film is a resin film.

9. An apparatus for maintaining a sterile room under a sterile condition, which comprises:

a HEPA filter incorporated within an air supply passage extending to the sterile room so as to filter the gas flowing therethrough;

a germ-removing filter comprising a filter substrate; and an antimicrobial material dispersedly mixed into the filter substrate, the antimicrobial material comprising antimicrobial fiber bonded with silver ions;

wherein the silver ions are bonded to the antimicrobial fiber through an ions exchange or chelating reaction and the total amount of the silver ions present in the filter is equivalent to the amount of silver ions present when the substrate contains at least 10 wt % of the antimicrobial fibers having all exchange groups or bonding groups exchanged or bonded with silver ions, wherein the germ-removing filter is disposed at least one of upstream of and inside the HEPA filter, and wherein the filter substrate of said germ-removing filter has a gas transmission side with a face which is laminated with a gas-permeable film.

10. An apparatus as defined in claim 9 including an upstream pre-filter, wherein said germ-removing filter is interposed between the upstream pre-filter and the HEPA filter.

11. An apparatus as claimed in claim 9, wherein the gas-permeable film is a resin film.

12. A germ-removing filter, comprising:

a filter substrate; and an antimicrobial material dispersedly mixed into the filter substrate, the antimicrobial material comprising antimicrobial fiber bonded with silver ions;

wherein the silver ions are bonded to the antimicrobial fiber through an ion exchange or chelating reaction and the total amount of the silver ions present in the filter is equivalent to the amount of silver ions present when the substrate contains at least 10 wt % of the antimicrobial fibers having all exchange groups or bonding groups exchanged or bonded with silver ions, wherein said antimicrobial fiber comprises ion exchange fiber in which silver ions are bonded through an ion exchange reaction with at least some of the ion exchange groups of a cation exchange fiber, and wherein said filter substrate has a gas transmission side with a face which is laminated with a gas-permeable resin film.

* * * * *